Figure 1:
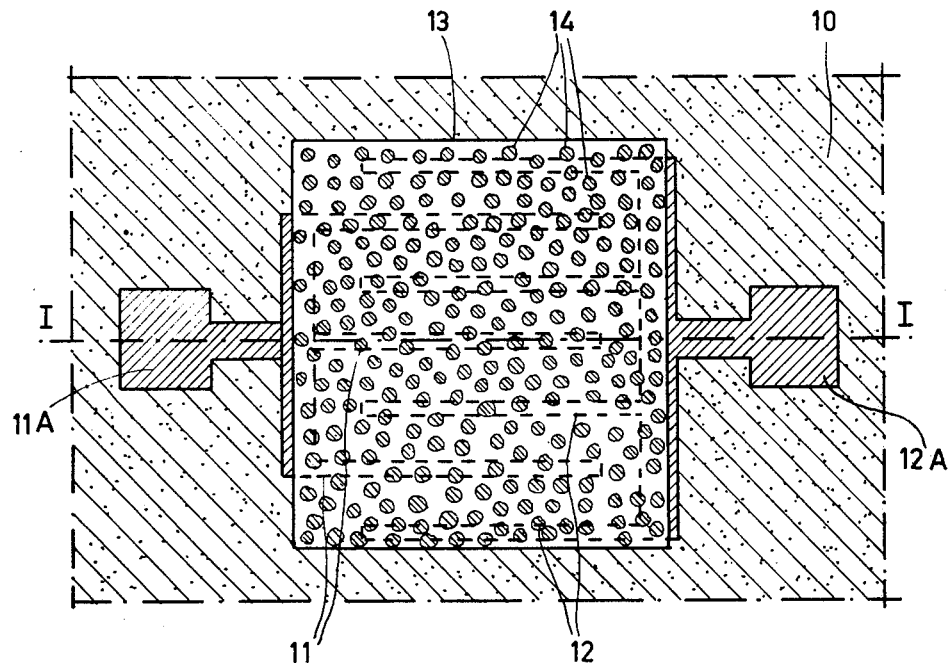

United States Patent [19]

Pompei et al.

[11] 4,016,524
[45] Apr. 5, 1977

[54] SENSOR FOR A GAS DETECTOR, IN PARTICULAR FOR SMOKE DETECTION

[75] Inventors: Jean Pompei, Noisy-Le-Roi; Bernard Lacroix, Paris; Francis Pierrot, Rueil-Malmaison, all of France

[73] Assignee: U.S. Philips Corporation, New York, N.Y.

[22] Filed: May 14, 1975

[21] Appl. No.: 577,314

[30] Foreign Application Priority Data

May 27, 1974 France .............................. 74.18212

[52] U.S. Cl. ............................... 338/34; 23/254 E; 200/61.03
[51] Int. Cl.² .......................................... H01L 7/00
[58] Field of Search ........... 338/34, 35; 340/237 R, 340/237 S; 73/23, 27; 23/254 R, 254 E, 255 E; 357/63, 64; 200/61.03

[56] References Cited

UNITED STATES PATENTS

| | | | |
|---|---|---|---|
| 3,625,756 | 12/1971 | Taguchi | 23/254 E X |
| 3,748,625 | 7/1973 | Bennewitz | 338/34 |
| 3,764,269 | 10/1973 | Oldham et al. | 73/23 X |
| 3,798,079 | 3/1974 | Chu | 357/63 |
| 3,831,432 | 8/1974 | Cox | 23/23 X |
| 3,864,659 | 2/1975 | Furuachi | 338/35 |
| 3,872,419 | 3/1975 | Groves et al. | 338/34 |
| 3,879,985 | 4/1975 | Maslen | 338/34 X |

*Primary Examiner*—C. L. Albritton
*Attorney, Agent, or Firm*—Frank R. Trifari

[57] ABSTRACT

Sensor for selectively detecting at least one constituent of a gaseous mixture in contact with the sensor. The sensor comprises a thin layer of a semiconductor material covered with a dielectric film formed with a large number of microscopic openings.

3 Claims, 2 Drawing Figures

SENSOR FOR A GAS DETECTOR, IN PARTICULAR FOR SMOKE DETECTION

The invention relates to a sensor for selectively detecting at least one constituent of a gaseous mixture which is in contact with the sensor, the operation of the sensor being based on the variation of its electrical resistance due to a reaction at the surface of the sensor.

The invention relates in particular, but not exclusively to a sensor for a smoke detector.

The gas detectors which are mainly used at present belong to two main categories: ionization detectors and oxide detectors.

In general, ionization detectors have satisfactory sensitivity and they operate comparatively selectively. Devices having these properties are expensive, however, because radioactive sources or lasers are used. In addition, the electric power consumption of the detectors is appreciable if they are used for continuous monitoring, and their use requires special precautions because of their noxiousness.

Manufacture of oxide detectors is simpler and they are used more frequently than ionization detectors. The operation of oxide detectors is based on variation of the electrical resistance of a porous layer or body consisting of a substance which is sensitive to contact with a given gas contained in the atmosphere to be analyzed or monitored. The said sensitive substance generally is a metal oxide or a mixture of metal oxides.

The oxide detectors made by the known methods have a serious disadvantage: their sensitivity and selectivity are substantially zero at room temperature. Useful sensitivity and selectivity are obtained only at comparatively high temperatures, of the order of several hundreds of degrees centigrade. Hence such detectors must be provided with a heater which is controlled by a thermostat and is arranged external to the sensitive element or is embedded in it, depending upon whether the element has a layered structure or a mass structure. The necessity of operation at elevated temperatures is a large disadvantage because of the energy consumption and the required temperature control, but also because the heating may give rise to explosion or fire if, for example, combustible gases or vapors, such as hydrogen, or vaporized hydrocarbons are to be detected.

Attempts have been made to enable the detector to be used at lower temperatures by searching for more sensitive substances. With respect to binary compounds of the type to which the metal oxides belong, an important improvement has already been obtained by the addition of substances which catalyze the action of these oxides, such as platinum, gold and palladium.

French Pat. No. 1,545,296 for example describes a detector which is used for detecting hydrogen or reducing gases and contains a sensor consisting of a layer of a semiconductive metaloxide which is supported by a dielectric substrate and is covered with a catalyst in the form of minute islands; a layer of conductive material is secured to the other surface of the substrate and serves as a heater. The operating temperature of the resulting thin-film sensor lies between 200° C and 380° C and in particular detection of hydrogen is possible at a temperature of only about 250° C.

By such a structure the advantage of the presence of a catalyst again is not fully utilized because it is in contact only with the thin oxide film and not incorporated therein.

Another type of detector in which the addition of activating substances to a semiconductor material of the metal oxide type is used is described in French Pat. No. 2,106,112. The sensor of this detector consists of a porous oxide material in which at least one activating substance is incorporated; the sensor furthermore has an internal winding for heating the oxide material.

A detector provided with such a sensor has a higher sensitivity than previous detectors of this category. Due to its large volume the sensor of the detector described in the latter patent specification has a large time constant.

Furthermore none of the sensors on the basis of oxide according to the said two patent specifications is protected against the influence of the water vapor which may be contained in the atmosphere to be analyzed or monitored. It is known, however, that fluctuating concentrations of water vapor produce a high degree of inaccuracy in detecting gases with oxide or ionization detectors.

It is an object of the present invention to provide a sensor for a gas detector that has a sensitivity which is considerably higher than that of known sensors of similar detectors without the necessity of raising the temperature of this sensor.

Another object of the invention is to provide a sensor which is less sensitive to the presence of water vapor in the gas mixture.

The invention is based on the operation of electrical double layers which are produced at the interfaces between certain materials when bounded together.

According to the invention a sensor for selectively detecting at least one constituent of a gaseous mixture in contact with the sensor, produced based on the variation in its electrical resistance by a reaction at the surface of the sensor, is characterized in that the sensor comprises a substrate on which is arranged a layer of a semiconductor material to which at least two electrodes are connected and which is at least partly covered with a layer of a dielectric material which is formed with a large number of microscopic openings.

The above expression "layer of a dielectric material formed with a large number of microscopic openings" is to be understood to mean a layer which leaves the said thin layer at least partly uncovered and which either is a continuous layer of porous structure or a layer divided into a plurality of discrete islands.

Advantageously the said layer of a semiconductor material consists of a binary compound of the metal oxide type and is sensitized by the presence of at least one activating substance in a surface layer.

Advantageously the dielectric material formed with the microscopic openings is hydrophobic.

A sensor for detecting gases (gases, vapors or smoke) according to the invention has several advantages in comparison with previously used sensors of the same category.

Such a sensor has a high sensitivity at room temperature.

Because the sensor need not be operated at an elevated temperature, temperature control can be dispensed with so that the detector is much less complex than the known detectors.

The absence of a heater eliminates any risk of explosion or ignition of the gas in contact with the sensor.

The sensor according to the invention also has the advantage of consuming very little energy due to the fact that in most cases the resistance of the thin semiconductor layer is high in the inoperative condition of the sensor (i.e., in the absence of the gas or gases to be detected) and also because the sensor is used at room temperature.

The high sensitivity of the sensor according to the invention is partly due to the strong adherence of the dielectric layer to the semiconductor layer, while the electric double layer at the interface probably has an enhancing effect in detection.

In a sensor according to the invention, with respect to the area where detection takes place a distinction must be made between two surfaces: on the one hand the assembly of the elementary surfaces of the semiconductor layer exposed by the openings in the dielectric layer and on the other hand the surface of the said dielectric layer.

For simplicity the semiconductor layer may be regarded as consisting of a plurality of elementary electrical resistors (each elementary resistor lying opposite an opening in the dielectric layer) which according to a complicated electrical circuit are interconnected by a network of connections of high conductivity (each connection being constituted by the electric double layer at the interface of one of the many areas of contact between the dielectric layer and the semiconductor layer).

The particles of the detected gas which are adsorbed at the surface of the semiconductor layer cause a reduction of the resistance of each elementary resistor by means of a well-known process of chemisorption. Due to the presence of the electric double layer the said reduction of the resistance of each elementary resistor results in a large and rapid reduction of the overall electrical resistance of the semiconductor layer measured between the electrodes of the sensor.

Due to the porous structure or the island structure of the dielectric layer the sensor according to the invention is not greatly affected by the presence of water vapor in the gas atmosphere to be detected or monitored, if the dielectric material is hydrophobic and the water vapor is not saturated. Because the dielectric layer consists of a hydrophobic material, at its surface electropositive particles of the water vapor are not adsorbed; hence the water vapor cannot influence the electric double layer.

If water is present in the form of non-saturated vapor, a device is used which is provided with two sensors according to the invention which have substantially the same resistance in the inoperative condition but different sensitivities in that, for example, one sensor has a semiconductor layer which is sensitized while the layer of the other sensor consists of a non-sensitized oxide.

Advantageously the introduction of the activating substance into the surface of the semiconductor layer is effected by diffusion of this substance by the action of a suitable heat treatment.

Another important advantage of the sensor according to the invention is that a large number of materials are suitable for use in such a sensor. A given semiconductor material for the semiconductor layer, to which at least one activating substance may have been added, can be combined with a given dielectric as the underlying layer to obtain a high sensitivity for a given gas or vapor. The possibility of combining various semiconductor materials and dielectric materials is related to the manner of providing the semiconductor layer and the dielectric layer by means of deposition in an ionized gas atmosphere, which process includes all methods in which a light-emitting discharge is maintained between two relatively polarized electrodes. This growth process for manufacturing devices having a semiconductor layer which is covered with a dielectric layer is described in our copending French patent application No. 74 18 214.

In an embodiment of a sensor according to the invention which may be used, for example, for detecting smoke in the atmospheric air the thin semiconductor layer consists of a binary compound of a metal and a metalloid, in particular zinc oxide or a combination of zinc oxide and copper oxide, while the overlying dielectric layer consists of a hydrophobic organic substance, such as polytetrafluoroethylene.

The oxide selected is deposited on a dielectric substrate, for example, a glass plate, to which previously two metal conductive areas have be applied which serve as electrodes. The oxide layer is then covered with the dielectric substance.

The oxide film is obtained by cathode sputtering of a target, which may consist of one or more metals, in an oxidizing atmosphere. The layer of polytetrafluoroethylene is obtained by cathode sputtering of a solid target of polytetrafluoroethylene in a neutral atmosphere and for a short time only so as to obtain a very thin film which as a result has the desired divided or porous structure.

During the entire treating cycle, in accordance with the method described in the aforementioned patent application, the structure in the discharge space must be insulated so that the surfaces of the layers are continuously at a floating potential which corresponds to the potential of the discharge plasma. In the case under consideration of a sensor provided on a glass substrate insulation does not give rise to problems and the substrate can directly be placed on the collecting electrode of the cathode sputtering apparatus.

The conditions under which the discharge takes place and which will be described hereinafter have the purpose of obtaining an oxide layer which in the inoperative condition has a high electrical resistance (of the order of several megohms between the conductive electrodes). This oxide film has n-type conductivity because it is obtained by cathode sputtering.

In order to increase the sensitivity to smoke of the zinc oxide film, the said surface regions advantageously include two activating substances, for example gold and cobalt, gold and bismuth, silver and antimony or silver and bismuth, etc. and in general two metals, one having a valency lower than that of the zinc (gold, silver) while the valency of the other is stable and is equal to or greater than that of zinc (cobalt, bismuth, antimony). For this purpose the following process is performed; first a thin film consisting of the two selected activating metals is deposited by cathode sputtering on the surface of the previously applied zinc oxide film, the target consisting of an alloy containing 2 to 5% of cobalt, bismuth, antimony, etc., the remainder being gold or silver, after which a suitable heat treatment is effected to diffuse the activating substances into the surfaces of the zinc oxide layer. The assembly can then be treated by applying the dielectric layer.

Obviously the list of activating substances with which the thin semiconductor layer can be doped is not restricted to gold or silver in conjunction with cobalt, bismuth or antimony. By an appropriate choice of the semiconductor material, of the activating substances with which it is doped and of the dielectric material of the coating a sensor having a high specific sensitivity for a given gas or vapor is obtained.

Figure 2:
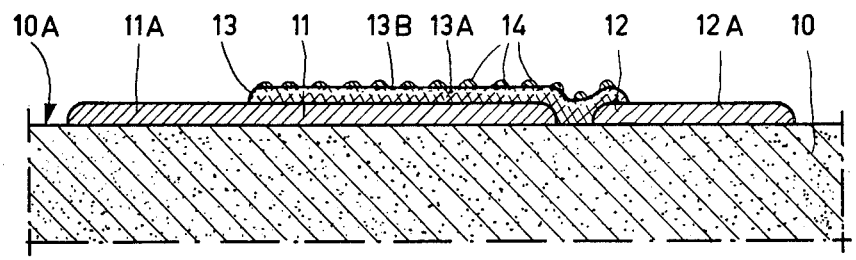

An embodiment of the invention will now be described, by way of example, with reference to the accompanying diagrammatic drawings, in which:

FIG. 1 is a plan view of a sensor according to the invention, for example, for use in a smoke detector, and FIG. 2 is a cross-seectional view taken on the line I — I of FIG. 1.

The sensor according to the invention is constructed on a dielectric substrate designated 10 in FIGS. 1 and 2. The substrate may be a small glass plate the thickness of which is equal to that of a window pane.

On a major surface 10A of the substrate 10 two conductive areas 11 and 12 are provided which may be shaped in the form of interdigitated combs and constitute the two electrodes of the sensor. The two areas may, for example, be a composite layer comprising a nickel-chromium-nickel layer and a gold layer.

The areas 11 and 12, with the exception of contact pads 11A and 12A, and the surrounding parts of the substrate 10 are covered by a layer 13 of a semiconductor material, for example a zinc oxide layer. The surface of the layer 13 includes activating substances provided by diffusion, for example gold-cobalt or gold-bismuth. Thus the layer 13 comprises two superposed portions: a lower portion 13A of pure zinc oxide and an activated upper portion 13B. A layer of a material formed with a large number of microscopic openings, for example a polytetrafluoroethylene layer shown in the Figures as a plurality of discrete islands 14, covers part of the layer 13 and may without any disadvantage extend slightly over the substrate 10 and the areas 11 and 12.

The surface area of the sensor according to the invention is about 50 mm$^2$. The conductive areas 11 and 12 are about 0.3 $\mu$m (0.2 to 0.4 $\mu$m) thick. The overall thickness of the layer 13 is about 0.15 $\mu$m (0.1 $\mu$m to 0.3 $\mu$m); the surface portion 13B has a very small depth, about $2.5.10^{-3}$ $\mu$m ($1.10^{-3}$ to $5.10^{-3}$ $\mu$m). The islands 14 which represent the film of dielectric material have a very small height, are very narrow and are closely spaced apart; however, their size is much smaller and they are much closer to one another than is shown in FIGS. 1 and 2.

The layer 13 and the film 14 in the form of islands are obtained by deposition from an ionized gas mixture as described in the aforementioned French patent specification.

The areas 11 and 12 are obtainable in a known manner by cathode sputtering, by deposition from vapor in a vacuum, by electrolytic means or by combinations of these techniques. The nickel-chromium-nickel layer, for example, may be obtained by vaporizing a nickel-chromium-nickel filament (80% nickel and 20% chromium) in a vacuum; this Ni-Cr-Ni layer is then chemically etched so as to obtain the configuration chosen for the layers 11 and 12, after which a layer of gold is provided on this structure by electrolysis.

The substrate 10 provided with the layers 11 and 12 is then placed on the aluminum collecting electrode of a cathode sputtering device of diode configuration, the target of which is a strip of nickel-plated steel coated with zinc provided either in solid form by melting, by electrochemical means and the like or in the form of a powder, arranged opposite the said collecting electrode.

The spacing between the target and the collecting electrode is about 80 mm (from 50 mm to 90 mm).

The discharge atmosphere is dry air at a pressure of $0.5.10^{-2}$ torr (from $10^{-3}$ to $10^{-2}$ torr). The supply voltage is a direct voltage of 2.5 kV (2 kV to 3 kV).

Thus a discharge current having a strength of about 1.6 mA (from 1.4 mA to 1.8 mA) per cm$^2$ of target area is produced, and on the substrate 10 a zinc oxide film 13 including stable oxygen vacancies is formed at a rate of 0.008 $\mu$m/minute (from 0.006 to 0.01 $\mu$m/minute).

After the formation of the layer 13 at least one activating substance may be incorporated in its surface regions.

In the embodiment under consideration gold-cobalt and gold-bismuth are used. First a gold-cobalt film or a gold-bismuth film is deposited on the surface of the film 13 by cathode sputtering of a target consisting of an alloy containing from 2 to 5% of cobalt or bismuth, the remainder being gold; the said cathode sputtering is effected in a device of diode configuration, the spacing between the target and the collecting electrode being about 80 mm (from 60 to 90 mm); the discharge atmosphere is air, the supply voltage is a direct voltage of 3 kV (from 2 to 4 kV), the current density is 0.2 mA (0.1 mA to 0.3 mA) per cm$^2$ of the target area, the sputtering period is about 1 second (from 0.5 to 1.5 second) with the result that the thickness of the said film is only a few Angstrom; subsequently the zinc oxide layer coated with a molecular film of gold-cobalt or gold-bismuth is subjected to a thermal aftertreatment at a temperature of 300° C (from 250° C to 350° C) in air for 2 minutes (from 1 to 3 minutes). During this aftertreatment the gold-cobalt or the gold-bismuth diffuse into the surface of the layer so as to form the active portion 13B.

Before the incorporation of the activating substances the electrical resistance of the layer 13, measured between the contact pads 11A and 12A, has a high value of the order of several megohms to several tens of megohms, depending upon the geometry of the sensor. After the provision of the gold-cobalt or gold-bismuth film the said resistance is reduced to a few ohms and subsequently after the thermal aftertreatment it has substantially regained its initial value.

To complete the sensor the dielectric substance must be provided to form the islands 14, in this embodiment polytetrafluoroethylene. For this purpose a second cathode sputtering process is effected. In known manner in an argon atmosphere a bombardment takes place of a target of solid polytetrafluoroethylene. The condition under which the polytetrafluoroethylene is deposited are for example: the two electrodes, one of which supports the target in the form of a small slab of polytetrafluoroethylene while the other supports the assembly to be coated, are made of aluminum and are spaced from one another by 50 mm (from 40 to 60 mm); the pressure in the space is stabilized at 0.8 torr (from 0.6 to 0.9 torr); the discharge is maintained by an alternating-current signal at a frequency of 30 MHz and the energy consumed is about 200 watts; the growth rate of the polytetrafluoroethylene then is about 0.003 $\mu$m/minute (from 0.002 to 0.005 $\mu$m/minute).

Under these conditions the structure has only to be left uncovered for three seconds to obtain a layer formed with microscopic openings (from 1 to 5 seconds).

A sensor manufactured in the above manner and having the above size in the inoperative condition (i.e., in a gaseous atmosphere containing no smoke) has a resistance of the order of 3 to 4 meg-ohms. This resistance is abruptly reduced to a few kilo-ohms as soon as the oxidizing smoke or vapor to be detected appears near the sensor.

Such a sensor may readily be incorporated in an electronic alarm circuit having an operational threshold which is determined in accordance with the value which its resistance may assume in situations of danger.

In known manner and in order to prevent water vapor which may be present in the ionized gas atmosphere from interfering with detection, an apparatus may be provided with two sensors according to the invention. In this case the two sensors must have about equal resistance in the inoperative condition but different sensitivities to the gas to be detected; for this purpose one of the electrodes is sensitized by means of an activating substance as described hereinbefore while the other sensor comprises only a pure oxide.

It should be mentioned that the invention is not restricted to the flat sensor structure described. The absence of a heater actually reduces the problems of the shape. For example, a sensor structure may be realized in which the substrate has the form of a rod of curved cross-section, in particular of circular cross-section.

On the other hand it should be mentioned that in all uses of the sensors in gas detectors they may be supplied either with direct current or with alternating current.

What is claimed is:

1. Sensor for selectively detecting at least one constituent of a gaseous mixture in contact with the sensor, the operation of this sensor being based on the variation of its electrical resistance by a reaction at the surface of the sensor, characterized in that the sensor comprises a substrate on which a layer of a semiconductor is provided to which are connected at least two electrodes and which is at least partly covered with a film of a dielectric material formed with a large number of microscopic openings.

2. Sensor as claimed in claim 1, characterized in that the semiconductor layer is a metal oxide which is superficially sensitized by two metallic activating substances, the valency of one of these metals being lower than that of the metal of the semiconductor whilst the valency of the other metal is at least equal thereto.

3. Sensor as claimed in claim 2, characterized in that the dielectric film formed with microscopic openings consists of a hydrophobic substance.

* * * * *